(12) United States Patent
Chung et al.

(10) Patent No.: US 6,479,555 B1
(45) Date of Patent: Nov. 12, 2002

(54) METHOD FOR INDUCING HEPATIC FIBROSIS BY REPEATED ADMINISTRATION OF ALLYLALCOHOL

(75) Inventors: Young-hwa Chung, #8-13 Sibum Apt., 50 Yoido-dong, Youngdeungpo-ku, 150-761, Seoul (KR); Sung Ae Jung, Seoul (KR); Jung A Kim, Seoul (KR); Neung Hwa Park, Ulsan-si (KR)

(73) Assignee: Young-hwa Chung, Seoul (KR)

( * ) Notice: Subject to any disclaimer, the term of this patent is extended or adjusted under 35 U.S.C. 154(b) by 0 days.

(21) Appl. No.: 09/598,880

(22) Filed: Jun. 21, 2000

(51) Int. Cl.⁷ .............................................. A61K 31/045
(52) U.S. Cl. ...................................... 514/724; 514/739
(58) Field of Search ................................... 514/724, 739

(56) References Cited

U.S. PATENT DOCUMENTS 4,118,506 A * 10/1978 Taninaka et al. ............ 424/277

OTHER PUBLICATIONS

"Stimulation of Collagen Alpha 1(I) Gene Expression is Associated . . . ", By Bedossa et al., published by Hepatology 1994 May;19(5):1262–71.

"Alcoholic Hepatitis", Charles L. Mendnhall ("Alcoholic Hepatitis" Disease of the liver, Seventh Ed. edited by Leon Schiff and Eugene R. Schiff. J. B. Lippincott Company, Philadelphia, 1993, pp. 856–874).

Chronic Hepatitis, By Kenneth P. Batts, M.D. et al. from, The American Journal of Surgical Pathology, 1995.

Experimental Models of Hepatic Fibrosis, By Hidekazu Tsukamoto, D.V.M. Ph.D. et al., from Seminars in Liver Disease, 1990; and Hepatoprotective Effects of Insulin–Like . . . , By Castilla–Cortazar, from Amer. Gastro. Assoc., 1997.

* cited by examiner

Primary Examiner—Dwayne C. Jones
Assistant Examiner—C. Delacroix-Muirheid
(74) Attorney, Agent, or Firm—Bachman & LaPointe, P.C.

(57) ABSTRACT

A method for inducing hepatic fibrosis by repeated administration of allylalcohol into animals and, more particularly, a method including administrating a specific dose, at an administration frequency and period to induce hepatic fibrosis.

3 Claims, 3 Drawing Sheets

METHOD FOR INDUCING HEPATIC FIBROSIS BY REPEATED ADMINISTRATION OF ALLYLALCOHOL

FIELD OF THE INVENTION

The present invention relates to a method for inducing hepatic fibrosis by repeated administration of allylalcohol in animals.

Particulary, the present invention relates to the method of allylalcohol treatment in terms of dosage, frequency and duration to induce the hepatic fibrosis.

The method of the present invention establishes an animal model which is useful in the investigation of a human chronic liver disease.

BACKGROUND

Hepatic fibrosis results from chronic liver damage induced by several causes and ultimately progresses to liver cirrhosis. This is very important to understand the mechanism of hepatic fibrosis in order to find ways to prevent and cure the liver cirrhosis. Chronic liver disease including liver chirrosis and liver cancer is one of the major causes of death in Korean adults.

One single most important cause for chronic liver disease is the viral hepatitis and 7% of total Korean population is estimated to be carriers of hepatitis B virus. The most typical histological view for the chronic hepatitis caused by B virus or C virus is an inflammatory necrosis such as a periportal piecemeal necrosis. The limiting plate of the periportal liver cell is then destroyed, and the necrotic inflammation is spread to hepatic parenchyma. The portal veins are expanded, and the inflammatory legions are formed between portal veins. This necrotic inflammation is accompanied by hepatic fibrosis and progresses to liver cirrhosis (Ishak, 1994; Philips & Poucell, 1981; Ishak, 1976).

Infection of humans with hepatitis virus leads to liver necrosis. With the continuous stimuli for over 6 months, humans develop liver sclerosis through the hepatic fibrosis. It is difficult to observe humans because it takes too long to develop from hepatic fibrosis to liver sclerosis (Liaw et al., 1988; McMahon et al., 1990).

Irreversibe accumulation of collagen takes place within 20 weeks in a mouse treated with carbon tetrachloride ($CCl_4$), and the induction period can be decreased to 8–10 weeks by pretreatment with phenobarbitol (Proctor & Chatamara, 1982). The animal model of liver sclerosis with repeated injection of carbon tetrachlodride is widely used. In this model, centrilobular necrosis is induced $CCl_3OO$ free radicals formed from $.CCl_3$ free radicals as a result of activation by cytochrome P450 enzymes prsent in the centrilobule. The mechanism of liver sclerosis caused by carbon tetrachloride is similar to but different from that of alcoholic liver diseases and viral hepatitis (Tsukamoto et al., 1990).

Recently, Song et al suggested that the expression pattern of TGF β1 caused by centrilobular necrosis and periportal necrosis may be different. The animal model with induced periportal hepatic necrosis by a common bile duct ligation can develop liver sclerosis in 4 weeks, and may be useful for studying chronic viral hepatitis (Paronetto, 1966; Bhunchet & Wake, 1992; Bhunchet et al., 1996). However, the technique is highly invasive and shows a high death rate making it difficult to use.

Another model using a heterologous serum develops hepatic fibrosis by immunological pathways without the liver cell necrosis, which is different from the process of the chronic viral hepatitis (Paronetto, 1966; Bhunchet & Wake, 1992; Bhunchet et al., 1996).

Moreover, metabolic heterogeneity has been reported that the various chemical and the enzymatic activities in the liver cell as well as the microstructure of hepatic parenchyma cells depand greatly on the distribution in the hepatic lobule (Nolte & Pette, 1972; Welsh, 1972; Guger et al., 1976; Kim et al., 1977; Schmidt, 1978; Hatoff et al., 1981). Therefore, we are in need of a better animal model for human hepatic fibrosis to investigate its development to choronic disease.

Allylalcohol ($CH_2$=CHCHOH) is a chemical with the molecular weight of 58.05. When injected into the intraperitoneal cavity, allylalcohol is absorbed, and oxidized to acrolein ($CH_2$=CHCHO) by alcohol dehydrogenase present in the periportal liver. Acrolein is an aldehyde known to cause intense liver toxicity, specifically inducing hepatic necrosis at the periportal(Parkinson, 1996).

However, this hepatic necrosis model is not suitable for studying human chronic liver diseases. It has been necessary develop the hepatic fibrosis model similar to that accompanying human hepatic necrosis.

The present inventors use allylalcohol, known to cause the hepatic necrosis selectively at the periportal with one injection, and have developed a method to produce hepatic fibrosis in the animal model. By repeated administration of allylalcohol, these inventors were able to produce hepatic fibrosis similar to that accompanying human chronic liver disease.

SUMMARY OF THE INVENTION

It is an object of this invention to provide a method for inducing hepatic fibrosis by repeated administration of allylalcohol in animals.

It is a further object of this invention to provide the animal model which is useful for the investigation of human chronic liver disease.

Further features of the present invention will appear hereinafter.

A: mild;

B: moderate;

C: severe; and

D: cirrhosis.

Figure 1:
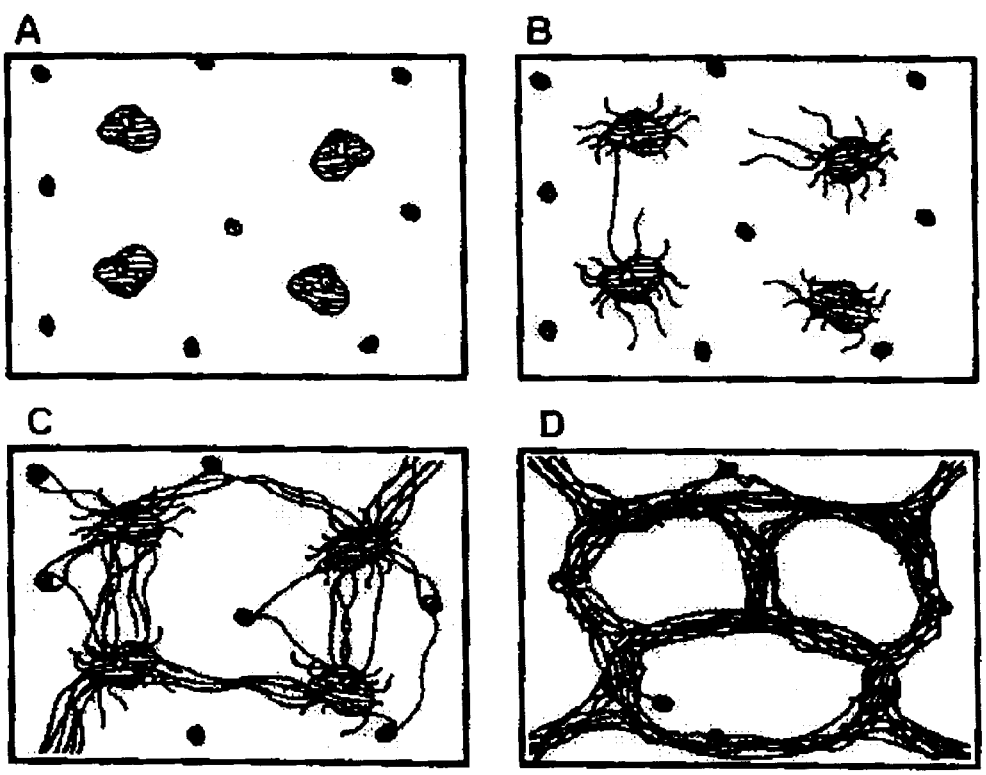
FIG. 1 shows an extent of hepatic fibrosis, where
Figure 2:
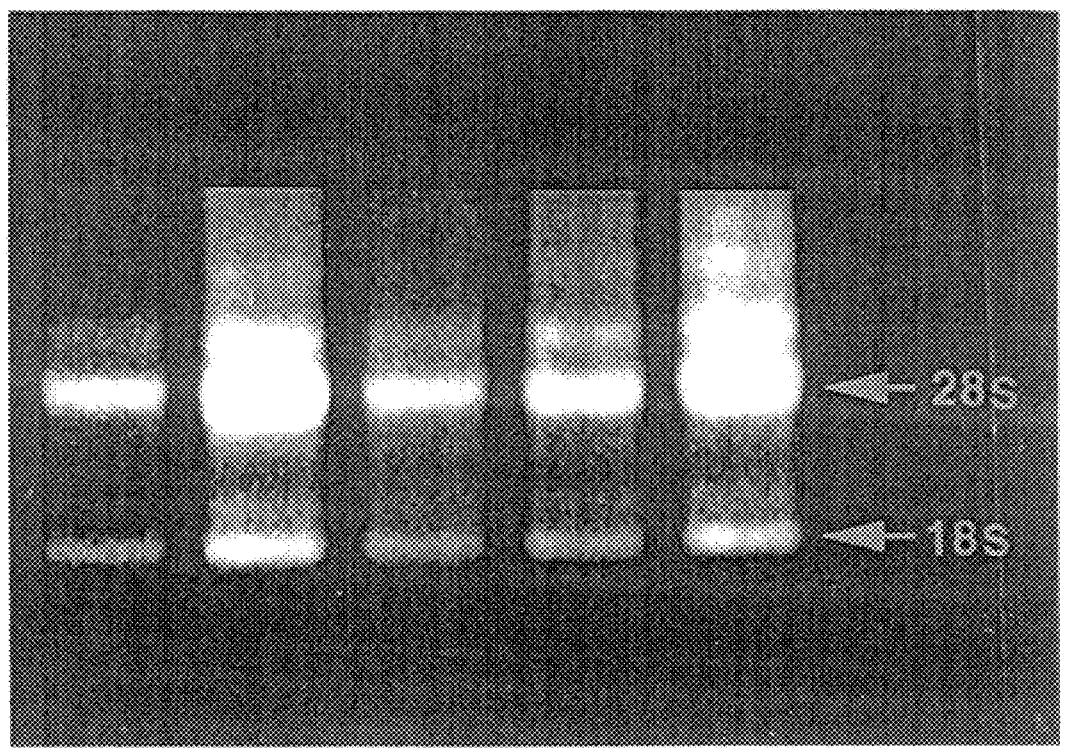

FIG. 2 shows an electrophoretic pattern of RNA stained with ethidium bromide.

Figure 3:
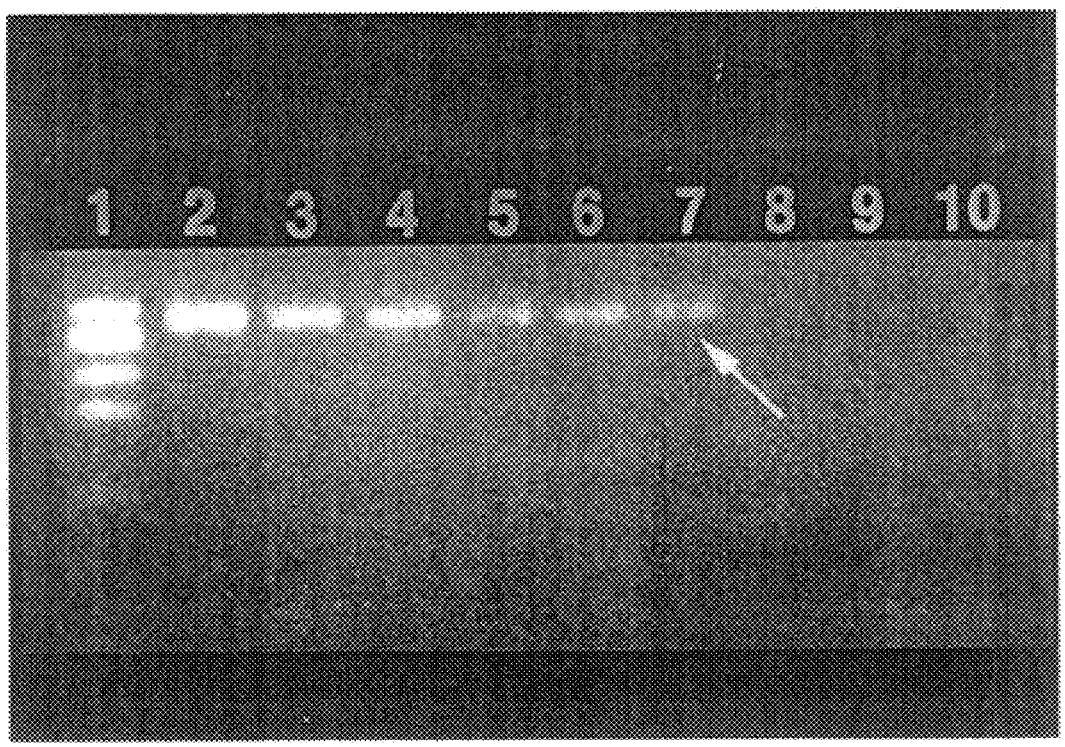

FIG. 3 shows a result of RT-PCR performed with TGF β1 RNA from the mouse liver tissue, where Lane 1: DNA size marker (X174/Hae III);

Lane 2: positive control;

Lane 3–9: samples; and

Lane 10: negative control.

DETAILED DESCRIPTION OF PREFERRED EMBODIMENTS

Hereinafter, the present invention is described in detail.

The present invention provides a method for inducing hepatic fibrosis in animals by a repeated injection of allylalcohol.

The animal used for the model in the present invention is preferably a white mouse. To induce hepatic fibrosis in the animal model, a dose of 0.5–0.7 mmole/kg of allylalcohol is preferably used for the white mouse.

The treatment with allylalcohol at a frequency of two or three times a week for a period of more than 8 weeks is preferable.

The present inventors have demonstrated by experiments that allylalcohol effectively induced hepatic fibrosis at the suggested dose, the treatment frequency and period.

In addition, the present inventors have determined an index of hepatic fibrosis by quantitatively analyzing liver tissues with the numerical scoring system. The index correlates well with TGF β1 mRNA expression and collagen content in the liver tissues indicating that the numerical index effectively estimates the extent of hepatic fibrosis.

Moreover, as seen in the white mouse model of the present invention, the collagen accumulation and the expression of TGF β1 mRNA increase as hepatic fibrosis progresses.

The result shows that TGF β1 is involved in the induction of hepatic fibrosis, and the expression of TGF β1 mRNA accompanies the development of fibrosis.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Reference Example 1
The Extent of Hepatic Fibrosis

Using semi-quantitative classification method of Batts and Ludwig, these inventors classified the extent of the hepatic fibrosis as "none" when the fibrosis was not observed, "moderate" when a microacrotism was observed at the periportal and the expansion of the portal was in progress, "severe" when the biseptal fibrosis connecting the portals or the portal and the centriolvein was observed, and "cirrhosis" when collagenous fibrous septa and the anagen node were observed.

Reference Example 2
The Quantification of Hepatic Fibrosis by the Numerical Scoring System In order to include width of fibrosis septa and fibrosis development in sinusoid as well as that between the portals, these inventors had quantified the extent of the fibrosis using the numerical scoring system reported by Castilla-Cortaza (1997) and Oberti (1997).

To systemically analyze the result of the numerical scoring system, these inventors also used the Image precessing and analysis system program (Leica Q500 MC, Leica Cambridge Ltd, Cambridge, U. K., 1994).

The length of septa was classified as score "4" when the septa showing fibrosis from one portal to the other is one whole length, score "3" for up to $2/3$, score "2" for up to $1/3$, and score "1" for less than $1/3$. For the width of septa, the score from 2–6 was given for the mean of widths of three different periportal septa, centriperiveinal septa and perinodal septa at four different sites.

The number for the width of septa was determined by measuring the fibrotic region of blood vessel in one node that score "4" when the whole node was filled with the fibrotic strand and a large number of the septa made the micronode, score "3" when the fibrosis region occupied up to $2/3$ of the whole node area, score "2" up to $1/3$, and score "1" when the fibrosis strand was little in the node.

Reference Example 3
Statistical Analyses

These inventors statistically analyzed the measured values with Mann-Whitney U Wilcoxen test, Mantel-Haenzel's chi squre test and Spearman's rank correlation coefficient. These inventors had statistically judged to be approved in case that p value was not more than 0.05.

Example 1
Animal Test
<1-1> Determination of a Dose of Allylalcohol for Inducing Hepatic Fibrosis Of the forty total Spraque Dawley male white mice (weight 150–200 g), 10 mice were used as a control group and 30 mice were treated with allylalcohol.

30 mice with treated allylalcohol were devided into three groups, each containing 10 mice. The 1st group was administered an injection with allylalcohol dissolved in saline solution with 0.3 mmole/kg into a peritoneal cavity twice a week. The 2nd and 3rd groups received 0.62 mmole/kg and 0.93 mmole/kg of allylalcohol, respectively, via the same method.

The animals were maintained 23° C. and 40% of relative humidity. The intensity of illumination was maintained for 12 hours from 6 A.M. to 6 P.M. They were sacrificed after 8 weeks.

A mouse in the 1st group injected with 0.3 mmole/kg of allylalcohol had severe hypertrophy and a vessel reproductive lesion, and was excluded from the statistic as a congenital malformation. Eight out of nine were shown to have mild hepatic fibrosis in the histological examination, and one moderate hepatic fibrosis. One from the 2nd group died within 8 weeks, and eight out of the remaining nine showed moderate hepatic fibrosis. Eight mice in the 3rd group died within 8 weeks, and the remaining 2 had severe hepatic fibrosis. The extent of hepatic fibrosis was proportional to the dose of allylalcohol, determining that as the dose of allylalcohol increased, more hepatic fibrosis was induced (p>0.01).

However, since the use of 0.93 mmole/kg of allylalcohol increased the death rate of mice, it was not suitable for inducing hepatic fibrosis. These inventors determined that the suitable dose for inducing hepatic fibrosis was 0.5–0.7 mmole/kg, and was preferable at about 0.62 mmole/kg (Table 1).

<Table 1>

TABLE 1

|  | None | mild | moderate | severe | death | Total |
|---|---|---|---|---|---|---|
| control | 10 |  |  |  | 0 | 10 |
| 1st group |  | 8 | 1 |  | 0 | 9 |
| 2nd group |  | 1 | 3 | 5 | 1 | 10 |
| 3rd group |  |  |  | 2 | 8 | 10 |

Mantel-Haenzel's chi squre test (p = 0.0005)

<1-2> Determination of Allylalcohol Treatment for Inducing Hepatic Fibrosis

The present inventors used total of 30 Spraque-Dawley male white mice, injected 0.62 mmole/kg allylalcohol into the peritoneal cavity twice a week, and sacrificed ten mice each time after 4 weeks, 8 weeks, and 16 weeks.

Histological examination of the mice liver tissues had shown that four out of ten receiving allylalcohol for 4 weeks had no evidence of hepatic fibrosis, and the remaining six with only mild hepatic fibrosis. Among the surviving nine out of 10 in the 8-week treatment group, one mild, three moderate, and the five severe cases were observed. Thus, eight out of nine have shown moderate or more intense hepatic fibrosis.

On the other hand, all the animals in the 16-week treatment group had moderate or more intense hepatic fibrosis, 5 of them showing hepatic cirrhosis with anagen node. The extent of hepatic fibrosis was demonstrated to be proportional to the period of allylalcohol treatment ($p<0.01$) (Table 2).

TABLE 2

|          | None | mild | moderate | severe | cirrhosis | death | Total |
|----------|------|------|----------|--------|-----------|-------|-------|
| control  | 10   |      |          |        |           | 0     | 10    |
| 4 weeks  | 4    | 6    |          |        |           | 0     | 10    |
| 8 weeks  |      | 1    | 3        | 5      |           | 1     | 10    |
| 16 weeks |      |      | 2        | 3      | 5         | 0     | 10    |

Mantel-Haenzel's chi squre test (p = 0.0005)

The extent of hepatic fibrosis determined by the numerical scoring system, all the animals in the control and 4-week group were less than 2 respectively, while all the animals in the 8-week and 16-week groups had higher than 7.

Therefore, the injection of allylalcohol for more than 8 weeks was preferable to induce hepatic fibrosis (Table 3).

TABLE 3

| Score    | 0  | 1  | 2 | 3 | 4 | 5 | 6 | 7 | 8 | 9 | 10 | 11 | 12 | 13 | 14 | death | Total |
|----------|----|----|---|---|---|---|---|---|---|---|----|----|----|----|----|-------|-------|
| Control  | 10 |    |   |   |   |   |   |   |   |   |    |    |    |    |    | 0     | 10    |
| 4 weeks  |    | 10 |   |   |   |   |   |   |   |   |    |    |    |    |    | 0     | 10    |
| 8 weeks  |    |    |   |   |   |   |   |   | 4 | 1 | 1  | 2  | 1  |    |    | 1     | 9     |
| 16 weeks |    |    |   |   |   |   |   | 1 | 1 |   | 1  | 1  | 3  | 2  | 1  | 0     | 10    |

Mantel-Haenzel's chi squre test (p = 0.0005)

<1-3> Specimen Collection and Storage

To collect a specimen, the white mouse was sacrificed 72 hours after final injection. The mouse was put under general anesthesia using diethylether, and its abdomen was cut open at suspine position. 7–10 ml of whole blood was withdrawn with a syringe treated with heparine, and the liver tissue was extracted.

For histological observation, the extracted liver tissue was fixed in 10% formalin solution. To extract total RNA, some of the liver tissue was immediately quick-freezing in liquid nitrogen and stored at −70° C.

The collected blood sample was left at room temperature for 30 min, centrifuged at 3,000 g for 10 min. The serum was devided into several fractions and stored at −70° C. until used.

Example 2
Measurement of Serum Alanine Aminotransferase (ALT) Activity

Serum alanine aminotransferase(hereinafter, as referred as "ALT") activity was measured by using the automatic analyzer (Hitach, 747/200 type), which is based on the spectrophotometric quantification of NADPH loss using lactic dehydrogenase as a coenzyme (Horder and Rej, 1983).

The ALT activity was 56.1±7.5 U/L, and increased to 69.6±39.8 U/L in control group, 63.8±9.6 U/L, and 75.5±15.9 U/L in the 4-week, 8-week and 16-week treatment groups, respectively. The ALT activity was shown to increase as the period of allylalcohol treatment increased.

It indicated that repeated injection of allylalcohol twice a week results in hepatic necrosis (Table 4).

TABLE 4

| Treatment period | ALT activity (U/L) |
|------------------|--------------------|
| control          | 56.1 ± 7.5         |
| 4 weeks          | 69.6 ± 39.8        |
| 8 weeks          | 63.8 ± 9.6         |
| 16 weeks         | 75.5 ± 15.9        |
| A, p < 0.05 : vs. control |           |

Example 3
Microscopic Analysis of Hepatic Fibrosis

The liver tissues of 30 mice obtained from the Example <1-2> were fixed in 10% formalin solution, stained with Masson's trichrome, and observed for the determination of fibrosis under light microscope.

The numbers of samples classified as normal, mild, moderate, severe and cirrhosis according to their extent of hepatic fibrosis were 4, 7, 5, 8 and 5, respectively.

Applying the numerical scoring system, score of 1.0±0 was obtained for the control group, 2.6±1 for the mild group, 9.0±1.7 for the moderate group, 9.8±1.5 for the severe group, and 12.4±1.5 for the cirrhosis group. A strong positive correlation was shown between the extent of fibrosis observed under microscope and the numerical scores ($r=0.9504$, $p<0.01$).

The numbers of tissue samples with score of 1–6, 7–10 and 11–14 determined by the numerical scoring system were 10, 9 and 10, respectively.

Example 4
Measurement of the Collagen Content

The collagen content of liver tissues was measured by dye-binding procedure of Jimenez. The liver tissue fixed in 10% formalin and embedded in paraffin was sliced by 15 um of thickness and put on a slide glass.

After the paraffin was removed by xylene and alcohol, the sample was stained with the saturated picric acid solution containing 0.01% fast green FCF (Fluka AG, NO 42053, Switzerland), left at room temperature for 15 min, and washed with a phosphate buffer until most color came off. The sample was restained with the saturated picric acid solution containing 0.04% fast green and 0.1% Sirius red F3B (Gurr BDH Chemical Ltd., NO 34149, Poole, England), left at room temperature for 30 min in the darkroom, and washed as before.

The stained tissue sample was transferred into the tube containing 1 ml solution with equal volume of 0.1% sodium hydroxide and methanol, and the tube was slowly shaken until the color dissolved completely. The absorbance of the colored solution was measured with a spectrophotometer. The wavelength for maximum absorbance was 630 nm for fast green, and 540 nm for Sirius red. Since fast green also absorbed a little (7.78%) at 540 nm, these inventors made calculations correcting for the factor.

The amount of collagen per unit protein was obtained with the formula 1 using the color equivalence of 3 OD/mg protein and 37 OD/mg collagen for fast green and Sirius red, respectively.

$$\mu g \text{ collagen/mg total protein} = \frac{\mu g \text{ collagen}}{\mu g \text{ collagen} + mg \text{ noncollagenal protein}} \quad \langle \text{formula 1} \rangle$$

wherein, absorbance 540 nm −

$$\mu g \text{ collagen} = \frac{7.78\% \text{ absorbance 630 nm}}{37}$$

$$mg \text{ noncollagenal protein} = \frac{\text{absorbance 630 nm}}{3}$$

The collagen content of control group was determined to be 86.1±30.0 ug collagen/mg protein, while it was 110.2±11.9 for the group with score 1–6 using the numerical scoring system, 131.4±30.0 for the group with score 7–10, and 158.2±94.2 ug collagen/mg protein for the group with score 11–14.

The collagen content of liver tissues with higher than score 7 increased significantly comparing to that of control group.

Distinct positive correlation was shown between the numerical score and the collagen content (r=0.4505, p<0.05) (Table 5).

TABLE 5

|  | Collagen content | P value |
|---|---|---|
| control (n = 10) | 86.1 ± 30.0 |  |
| Score 1–6 (n = 10) | 110.2 ± 11.9 | 0.0696 |
| Score 7–10 (n = 9) | 131.4 ± 30.0 | 0.0055 |
| Score 11–14 (n = 10) | 158.2 ± 94.2 | 0.0019 |
| P value, vs. control | | |

The collagen contents of liver tissues in the animals treated for 4 weeks, 8 weeks and 16 weeks were 110.2±11.9, 132.5±29.3, and 157.2±94.7, respectively(Table 6). Significant increase was observed for the animals treated for more than 8 weeks, compared to the control.

TABLE 6

|  | Collagen content | P value |
|---|---|---|
| control (n = 10) | 86.1 ± 30.0 |  |
| 4 weeks | 110.2 ± 11.9 | 0.0696 |
| 8 weeks | 132.5 ± 29.3 | 0.0043 |
| 16 weeks | 157.2 ± 94.7 | 0.0025 |
| P value, vs. control | | |

Example 5

Semi-quantitative Measurement of TGF β1 mRNA Expression in the Liver Tissue

<5-1> Extraction of Total RNA in the Liver Tissue

Total RNA of the mouse liver tissue stored at −70° C. was extracted by one-step method using acid guanidinium thiocyanate-phenol-chloroform (AGPC, 1987) of Chomczynski and Sacchi. 50–100 ug of the frozen liver tissue was homogenized in 1 ml of denaturing solution (4 M guanidinium thiocyanate, 25 mM sodium citrate, pH 7, 0.5% sarcosyl, 0.1 M 2-mercapto ethanol).

After the addition of 1 ml of phenol and 100 ul of chloroform were added to it, the homogenate was shaken thoroughly for 15 sec, left at 4° C. for 5 min, and centrifuged at 12,000 g and 4° C. for 15 min. The supernatant (aqueous phase) was withdrawn, mixed with equal volume of isopropanol, left at 4° C. for 15 min, and centrifuged as before.

RNA pellet was collected, washed with 75% ethanol twice, and centrifuged at 7,500 g and 4° C. for 8 min to remove ethanol. RNA pellet was dried under vacuum using the Speed Vac concentrator at −70° C. for 15 min. The dried RNA was dissolved in 20 ul of deionized distilled water (DDW) treated with 0.1% di-ethyl-pyro-carbonate (DEPC), and stored at −70° C. RNA concentration was determined by spectrophotometric measurement of absorbance at 260 nm. When the absorption ratio of $A_{260}/A_{280}$ used as an index of purity, exceeds 1.8, RNA samples were considered pure.

In addition, the purity of the extracted RNA was examined by agarose gel electrophoresis performed on 10 ug total RNA using MOPS(4-morpholinepropane sulfonic acid) buffer and ethidium bromide staining (FIG. 2)

<5-2> Quantification of TGF β1 mRNA in the Liver Tissue Using RT-PCR

<5-2-1> cDNA Synthesis

For the synthesis of cDNA of TGF β1 mRNA, 2 ul of total RNA extracted from the mouse liver tissue was mixed with 10 unit of Molony murine leukemia virus reverse transcriptase(M-MuLV RT), 100 ng of oligo-$dT_{15}$, 1 ul of dNTP (dGTP, dATP, dTTP, dCTP), RNase inhibitor 20 unit, 0.5 ul of 100 mM dithitritol (DTT) and 4 ul of 5×buffer solution, and total volume of the reaction mixture was adjusted to 20 ul by adding 0.1% DEPC-treated DDW.

The reaction mixture was heated at 37° C. for 90 min and 95° C. for 5 min, and rapidly cooled down on ice. 80 ul of DDW was added to this cDNA mixture which was then used as a PCR template.

<5-2-2> Primer Synthesis

For amplification of TGF β1 cDNA template, a sense-primer represented by SEQ ID NO.1 and an antisense-primer represented by SEQ ID NO.2 was synthesized. The position and the PCR product size of the primer set were described in Table 7. The concentration of the synthesized primer was adjusted to 10 pmole/ul by dissolving in TE buffer solution and stored at −20° C. until used.

TABLE 7

| Primer set | Nucleotide position | Product size |
|---|---|---|
| Sense | 1267–1291 | 298 bp |
| Antisense | 1564–1540 |  |

<5-2-3> Semi-quantitative Measurement of TGF β1 mRNA in the Liver Tissue Using PCR cDNA solution was diluted by two times until the concentration was to be $2^{-1}, 2^{-2}, 2^{-3}, \ldots,$ and $2^{-10}$, and used as PCR templates. 50 ul total of PCR reaction solution contained 4 ul of cDNA template solution, 1 unit of Taq DNA polymerase, each of 1 ul the antisense and the sense primer, 1 ul of dNTP, 5 ul of 10×buffer solution (containing 2.5 mM $MgCl_2$) and 37.7 ul of DDW.

To prevent vaporization of the sample at high temperature, 20 ul of mineral oil was added to the reaction mixture. PCR reaction was performed with PCR automated thermal cycler (Perkin Elmer) by using a hot start method. The hot start method included a denaturation step at 94° C. for 4 min, and the primer annealing and extension step at 65° C. for 15 min (at this step, Taq DNA polymerase was added after 10 min).

The reaction system then underwent 35 cycles of heating 94° C. for 45 sec, 60° C. for 45 sec, and 72° C. for 2 min, and the extension step was completed with 5 min heating at 72° C. In the RNA synthesis, negative control was distilled water, and positive control was 1 ul of TGF β1 cDNA fragment solution provided from a Clontech Laboratory.

The amplified PCR product mixed with 6×DNA loading buffer (0.25% bromophenol blue, 0.25% xylene cyanol, 30% glycol) was analyzed by electrophoresis using 2% agarose gel containing 1 ul ethidium bromide with 1×TBE buffer solution(89 mM tris-borate, 2 mM EDTA). After the electrophoresis at 100 volt for 60 min, UV transilluminator was used to establish the visible band(FIG. 3).

The expression of TGF β1 mRNA in the liver tissue, was 3.0±1.6 unit/total RNA 2 ug for the positive control. It was 4.7±2.4 for the group with score 1–6 by the numerical scoring system was, 5.8±1.5 for the group with score 7–10, and 5.7±2.0 for the group with 11–14, showing that TGF β1 mRNA expression increased as more fibrosis developed by repeated injection of allylalcohol. The increase in TGF β1 mRNA expression was statistically significant for the group with higher than score 7.

A notable correlation was observed between the numerical score and the expression of TGF β1 mRNA in the liver tissue (r=0.4398, p<0.05)(Table 8).

TABLE 8

|  | TGF β1 mRNA (unit/total RNA 2 ug) | P value |
|---|---|---|
| control (n = 10) | 3.0 ± 1.6 |  |
| Score 1–6 (n = 10) | 4.7 ± 2.4 | 0.0551 |
| Score 7–10 (n = 10) | 5.8 ± 1.5 | 0.0009 |
| Score 11–14 (n = 10) | 5.7 ± 2.0 | 0.0076 |
| P value, vs. control |  |  |

In addition, the expression level of TGF β1 mRNA in the liver tissue from animals treated for 4 weeks, 8 weeks and 16 weeks was 4.7±2.4, 5.8±1.0 and 5.7±2.3, respectively. The group prescribed for over 8 weeks represented the notable increase, and the content of TGF β1 mRNA in the liver tissue had a distinct correlation with the collagen content (r=0.4009, p<0.05)(Table 9).

TABLE 9

|  | TGF β1 mRNA (unit/total RNA 2 ug) | P value |
|---|---|---|
| Control (n = 10) | 3.0 ± 1.6 |  |
| Score 1–6 (n = 10) | 4.7 ± 2.4 | 0.0551 |
| Score 7–10 (n = 10) | 5.8 ± 1.0 | 0.0009 |
| Score 11–14 (n = 10) | 5.7 ± 2.3 | 0.0076 |
| P value, vs. control |  |  |

INDUSTRIAL APPLICABILITY

The present invention relates to a method for inducing hepatic fibrosis by repeated administration of allylalcohol in animals.

The present invention has demonstrated that hepatic fibrosis is induced by administration of allylalcohol with a dose of 0.5–0.7 mmole/kg twe or three times a week for more than 8 weeks.

The method of the present invention establishes an animal model useful for the investigation of the chronic hepatic disease which progresses through periportal hepatic necrosis and fibrosis.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for inducing hepatic fibrosis selectively at a periportal zone by repeatedly administering to an animal an effective amount of allylalcohol in an interval of 2–3 times a week for 8–16 weeks.

2. The method according to claim 1, wherein the allylalcohol is administered in an amount of 0.5–0.7 mmole/kg.

3. The method according to claim 1, wherein the animal is a white rat.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: sense-primer

<400> SEQUENCE: 1
cttcagctcc acagagaaga actgc                                    25

<210> SEQ ID NO 2
<211> LENGTH: 25
<212> TYPE: DNA
<213> ORGANISM: Artificial Sequence
<220> FEATURE:
<223> OTHER INFORMATION: antisense-primer

<400> SEQUENCE: 2
cacgatcatg ttggacaact gctcc                                    25